(12) United States Patent
Dalebout et al.

(10) Patent No.: US 8,216,155 B2
(45) Date of Patent: Jul. 10, 2012

(54) BODILY FLUID SAMPLING SYSTEMS, METHODS, AND DEVICES

(75) Inventors: Corey Dalebout, Lincoln, CA (US); Lincoln Jolley, Stansbury Park, UT (US)

(73) Assignee: Glucor Systems, LLC, Orem, UT (US)

( * ) Notice: Subject to any disclaimer, the term of this patent is extended or adjusted under 35 U.S.C. 154(b) by 565 days.

(21) Appl. No.: 12/252,041

(22) Filed: Oct. 15, 2008

(65) Prior Publication Data

US 2009/0099431 A1   Apr. 16, 2009

Related U.S. Application Data

(63) Continuation-in-part of application No. 12/036,787, filed on Feb. 25, 2008, now abandoned, which is a continuation-in-part of application No. 11/765,888, filed on Jun. 20, 2007, now abandoned.

(60) Provisional application No. 60/805,426, filed on Jun. 21, 2006.

(51) Int. Cl.
*B65D 81/00* (2006.01)
*A61B 5/00* (2006.01)

(52) U.S. Cl. .......... 600/584; 600/347; 600/576
(58) Field of Classification Search .......... 600/347, 600/573, 576, 584
See application file for complete search history.

(56) References Cited

U.S. PATENT DOCUMENTS

| | | | |
|---|---|---|---|
| 3,115,138 A | 12/1963 | McElvenny | |
| 4,429,693 A | 2/1984 | Blake | |
| 4,673,386 A | 6/1987 | Gordon | |
| 5,368,029 A | 11/1994 | Holcombe | |
| 5,374,401 A | 12/1994 | Von Berg | |
| 5,759,160 A | 6/1998 | Neese | |
| 5,961,472 A | 10/1999 | Swendson | |
| 6,159,164 A | 12/2000 | Neese | |
| 6,224,561 B1 | 5/2001 | Swendson | |
| 6,394,979 B1 | 5/2002 | Sharp et al. | |
| 6,616,632 B2 | 9/2003 | Sharp et al. | |
| 6,623,702 B2 | 9/2003 | Allen et al. | |
| 7,299,081 B2 | 11/2007 | Mace et al. | |
| 2002/0185384 A1 | 12/2002 | Leong et al. | |
| 2004/0116830 A1* | 6/2004 | Trudeau et al. | 600/584 |
| 2005/0136501 A1 | 6/2005 | Kuriger | |
| 2005/0277850 A1 | 12/2005 | Mace | |
| 2007/0129618 A1* | 6/2007 | Goldberger et al. | 600/347 |

(Continued)

OTHER PUBLICATIONS

Office Action dated Jan. 4, 2008, 14 pages, U.S. Appl. No. 11/765,888.

(Continued)

*Primary Examiner* — Max Hindenburg
*Assistant Examiner* — Emily Lloyd
(74) *Attorney, Agent, or Firm* — Workman Nydegger

(57) ABSTRACT

A fluid sampling system is disclosed comprising a fluid drawing device, a fluid sampling device, and an analysis device. The fluid drawing device can be used to draw bodily fluid into a sample port of an IV tube. The fluid sampling device can be used to access the sample port to obtain a fluid sample. The fluid sampling device can include a test strip housing for receiving a test strip therein. Extending from an end of the test strip housing is a blunt cannula that can be inserted into the sample port to obtain the fluid sample and communicate the fluid sample to the test strip. The test strip housing is configured to allow the one end of the test strip to be received within an analysis device to facilitate analysis of the fluid sample.

18 Claims, 6 Drawing Sheets

U.S. PATENT DOCUMENTS

2008/0045862 A1 2/2008 Dalebout et al.
2008/0255473 A1 10/2008 Dalebout et al.

OTHER PUBLICATIONS

Office Action dated Jul. 9, 2008, 16 pages, U.S. Appl. No. 11/765,888.

Better Living Now. ACCU-CHECK Comfort Curve Test Strips [online], Apr. 16, 2006 [retrieved on Feb. 16, 2011], Retrieved from the Internet: <URL: www.betterlivingnow.com/products/proddetail.cfm?ndc=50924038110>.

Aragon, Evaluation of Nursing Work Effort and Perceptions About Blood Glucose Testing in Tight Glycemic Control, American Journal of Critical Care, vol. 15:370-377, No. 4, Jul. 2006.

Greet Van den Bergh, et. al., Intensive Insulin Therapy in Critically Ill Patients, The New England Journal of Medicine, vol. 345:1359-1367, No. 19, Nov. 8, 2001.

Office Action mailed Aug. 18, 2010 under U.S. Appl. No. 12/036,787.

* cited by examiner

BODILY FLUID SAMPLING SYSTEMS, METHODS, AND DEVICES

CROSS-REFERENCE TO RELATED APPLICATIONS

This application is a continuation-in-part of U.S. patent application Ser. No. 12/036,787, filed Feb. 25, 2008 now abandoned, entitled SYSTEMS, METHODS, AND DEVICES FOR SAMPLING BODILY FLUID, which is a continuation-in-part of U.S. patent application Ser. No. 11/765,888, filed Jun. 20, 2007 now abandoned, entitled SYSTEMS, METHODS, AND DEVICES FOR SAMPLING BODILY FLUID, which claims the benefit of U.S. Provisional Application No. 60/805,426, filed Jun. 21, 2006, entitled BLOOD SAMPLING SYSTEM, all of which are hereby incorporated by reference in their entireties.

BACKGROUND

1. Technical Field

The invention relates to medical systems, methods, and devices. More specifically, the invention relates to systems, methods, and devices for sampling bodily fluid.

2. Relevant Technology

In some medical procedures, the condition of a patient can require that an intravenous/intra-arterial tube or catheter be inserted into a blood vessel. The patient's blood vessel can be connected by the tube to a source of fluid, such as a medicament. The tube can also be connected to a pressure transducer that senses the pressure within the patient's blood vessel.

In critical care situations, it can be necessary to periodically obtain samples of the patient's bodily fluids, such as blood. For procedures carried out using a needle stick, the likelihood of a healthcare worker being inadvertently stuck can increase, thereby increasing the risk of infection from a contaminated needle. Rather than stick a patient with a needle each time blood must be drawn, blood can be drawn through the tube already connected to the patient's blood vessel. Since the tube connected to the patient's blood vessel can contain fluid other than blood, such as saline solution and medication, it is useful to draw the patient's blood up into the tube to a sample site so that a blood sample can be obtained which is substantially unadulterated by the fluid that is being supplied to patient through the tube. After the substantially unadulterated blood has been drawn up the tube to the sampling site, the blood sample can be accessed through the sampling site and collected into a sample container.

In 2001, a study of 1548 patients was performed to demonstrate the effects of "intensive insulin therapy" on mortality and morbidity. See Greet Van den Bergh, et. al., *Intensive Insulin Therapy in Critically Ill Patients*, The New England Journal of Medicine, Vol. 345:1359-1367, No. 19, Nov. 8, 2001. The study showed that patients with tightly controlled blood glucose levels (between 80-110 mg/dl) had remarkably improved outcomes. Overall mortality was decreased by 34%, blood stream infections decreased by 46%, acute renal failure requiring dialysis or hemofiltration decreased by 41%, and the median number of red cell transfusions decreased by 50% as well as requiring less time on the ventilator and fewer days in the ICU.

The medical community has been striving for successful implementation of intensive insulin therapy because of its documented benefits. In order to implement this therapy, patients may have their fingers stuck for glucose readings every hour for days, weeks and even months. This can cause a significant amount of pain and torment to be inflicted on the patients. Additionally, the costs associated with repeated glucose level monitoring, in both dollars and nursing time, can be considerable.

For example, in a 2006 study of a level 1 trauma center, the time required to measure blood glucose levels and adjust insulin doses accordingly ranged from three to eight minutes, with an average time nearing five minutes. See Aragon, *Evaluation of Nursing Work Effort and Perceptions About Blood Glucose Testing in Tight Glycemic Control*, American Journal of Critical Care, Vol. 15:370-377, No. 4, Jul. 2006. Based upon this average time as well as the average compensation for nurses, the study determined that a hospital's annual nursing cost for intensive insulin therapy is about $182,488. The study also found that about 75% of nurses use an arterial catheter to obtain the blood samples while about 25% of nurses used finger sticks to obtain the needed blood samples. Using these proportions and the supply costs for each method, including lancets, syringes, and test strips, the study found that a hospital's annual supply cost for intensive insulin therapy is about $50,670.

In addition to the time and financial costs associated with intensive insulin therapy, the study also found that nurses feel that the current testing methods are difficult and require too much work. As a result some nurses try to keep their patients off intravenous insulin if at all possible, despite the documented benefits. A large majority of the nurses surveyed, 86%, indicated that an easier or more automated form of measurement was needed, while 76% indicated that they would be willing to devote an intravenous access for that purpose.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Example embodiments of the medical system described herein can enable the user more freedom to deal with positional lines, obtain glucose readings and can save time by initiating the testing process. This system can accomplish various significant improvements over the current testing methods while still garnering the significant benefits of intensive insulin therapy and being adaptable for use in nearly all hospitals. One benefit of the present invention is that it can reduce pain and discomfort of patients by reducing repeated finger pricking and venous sticks to obtain lab samples. Further, the present invention can decrease the time necessary for practitioners to ascertain a patient's glucose levels and obtain blood samples for lab use. Another benefit of the present invention is that it can decrease the risk to practitioners and patients by reducing the need for needles used in the transfer of blood from sample ports to test strips, and those used with phlebotomy. Additionally, the present invention can decrease cross contamination risk by utilizing a contained blood sample within the sampling device.

Embodiments of the present invention described herein relate to a fluid sampling system. The fluid sampling system can include a fluid drawing device, a fluid sampling device, and a glucometer to analyze the fluid sample. The fluid drawing device of the fluid sampling system can be used to draw bodily fluid, such as blood, from a patient injection site into an IV tube or catheter. After the fluid has been drawn into the IV tube, the fluid sampling device can be introduced into a sample port of the IV tube to retrieve a sample of the bodily fluid. After a fluid sample has been retrieved, the fluid sample can be analyzed with an analysis device, such as a glucometer, that can be configured to accommodate the test strip and/or the fluid sampling device.

The fluid sampling system of the present invention can provide a safe method of obtaining a sample of bodily fluid from a patient. For instance, the fluid sampling system can reduce the need to use needles each time a blood sample is needed, which in turn can reduce the pain and discomfort a patient experiences each time he or she is pricked. Further, the possibility that a healthcare worker will be pricked with a contaminated needle can be reduced with use of the fluid sampling system. Additionally, the fluid sampling system can be simple to use, thus allowing healthcare workers to focus on other aspect of the patient's treatment.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
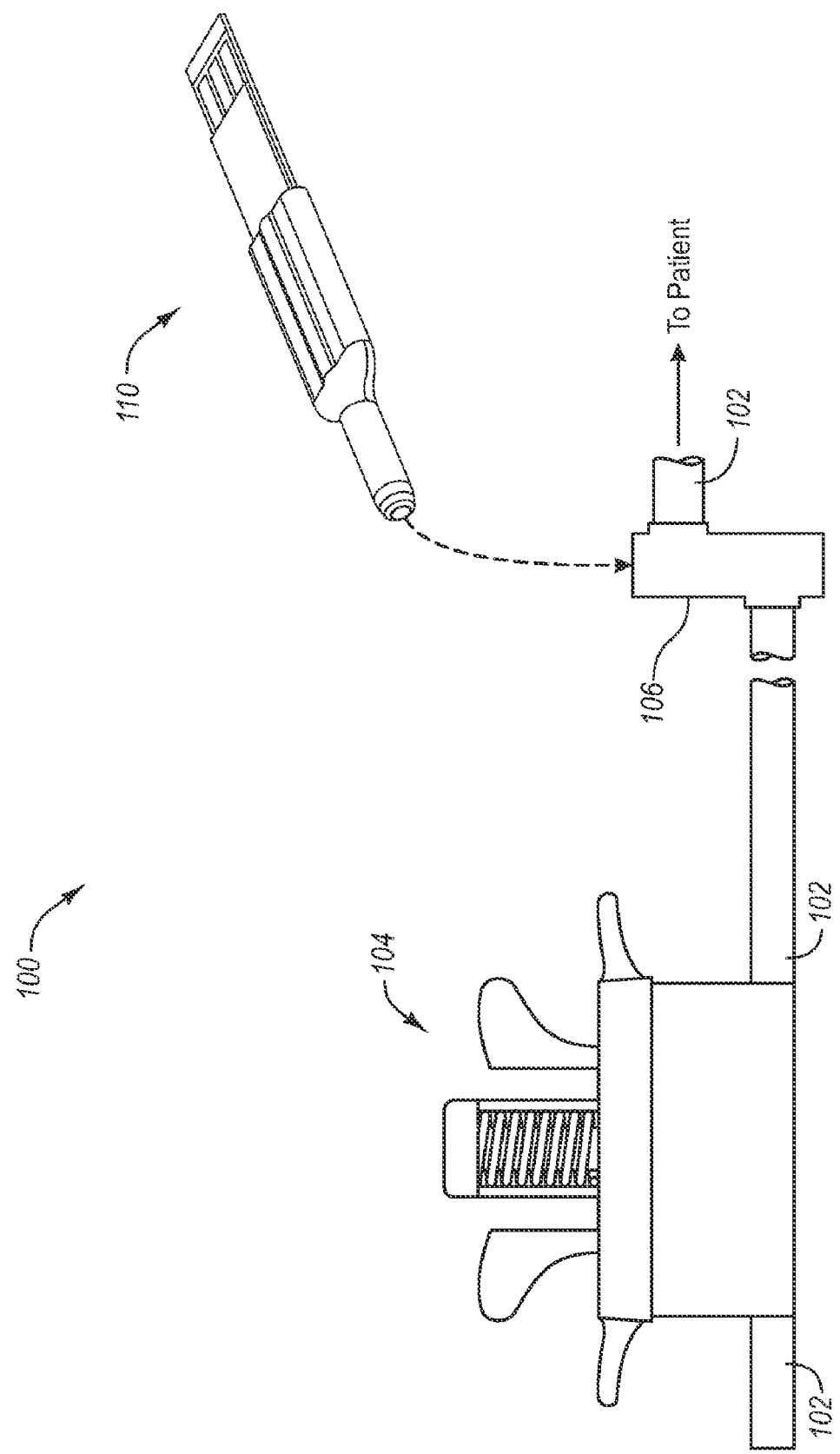
FIG. 1 illustrates a fluid sampling system according to one embodiment of the present invention.

Embodiments of the present invention described herein relate to a fluid sampling system. The fluid sampling system can include a fluid drawing device, a fluid sampling device, and a glucometer to analyze the fluid sample. Other standard medical equipment used in conjunction with these elements can include a pressure transducer, an IV stand, a pressure bag, saline solution, IV tubing, and a vascular access, such as an IV, Arterial Line, or a Central Venous Line, for example.

The fluid drawing device of the fluid sampling system can be used to draw bodily fluid, such as blood, from a patient injection site into an IV tube or catheter. After the fluid has been drawn into the IV tube, the fluid sampling device can be introduced into a sample port of the IV tube to retrieve a sample of the bodily fluid. After a fluid sample has been retrieved, the fluid sample can be analyzed with an analysis device, such as a glucometer, that can be configured to accommodate the test strip and/or the fluid sampling device.

The fluid sampling system of the present invention can provide a safe method of obtaining a sample of bodily fluid from a patient. For instance, the fluid sampling system can reduce the need to use needles each time a blood sample is needed, which in turn can reduce the pain and discomfort a patient experiences each time he or she is pricked. Further, the possibility that a healthcare worker will be pricked with a contaminated needle can be reduced with use of the fluid sampling system. Additionally, the fluid sampling system can be simple to use, thus allowing healthcare workers to focus on other aspect of the patient's treatment.

In the disclosure, reference is made to the use of a test strip with a fluid sampling device. As used in the disclosure and the claims, a test strip can be any device capable of detecting attributes of a fluid sample. By way of example and not limitation, a test strip can comprise a substrate with an absorbent material and a reagent disposed thereon. Alternatively, a test strip can comprise electrical leads or connections which can communicate various properties of a fluid sample to an analysis device, such as a glucometer. It will be appreciated that a test strip can also comprise a combination of any one or more of a reagent, an absorbent material, and electrical connections. While reference to specific types of test strips is made herein, it will be appreciated that the specific test strips referred to are provided merely as examples and it is contemplated that the present invention can utilized or adapted for use with other types of test strips not specifically referred to herein. For example, a test strip having an absorbent material and/or a reagent can be replaced with a test strip having electrical connections.

In the disclosure, reference is also made to IV tubes used with the fluid sampling system. As used in the disclosure and claims, an IV tube can include, but is not limited to, a central line, a PICC line, a feeding tube, a drain tube, or nearly any type of fluid pathway or catheter, including urinary, pulmonary artery, or cardiac catheters.

In one example embodiment, an IV tube is connected to a pressure bag (or a pressure transducer) at one end thereof, while the other end of the IV tube is in fluid communication with a patient injection site. A fluid drawing device can be connected to the IV tube between the pressure bag and the patient such that fluid flowing through the IV tube also flows through the fluid drawing device or is otherwise in fluid communication with the fluid drawing device. In addition, the IV tube also includes a sample port between the fluid drawing device and the patient. The fluid sampling device can be inserted into the sample port in order to take a sample of the fluid in the IV tube.

When the fluid sampling system is configured as described above, a user, such as a doctor or nurse, can take a sample of a patient's bodily fluid, such as blood, by activating the fluid drawing device, which draws the bodily fluid into the IV tube past the sample port. The user can then insert the fluid sampling device into the sample port to retrieve a sample of the bodily fluid. When a sufficient fluid sample has been retrieved, the fluid sampling device can be removed from the sample port. The fluid sampling device can be configured to have a test strip disposed therein. When the bodily fluid enters the fluid sampling device from the sample port, the bodily fluid can be absorbed by or come into contact with the test strip. The sample of bodily fluid can then be analyzed by an analysis device, such as a glucometer.

As seen in FIG. 1, an exemplary embodiment of the fluid sampling system 100 can include an IV tube 102, a fluid drawing device 104, a sample port 106, and a fluid sampling device 110. Fluid drawing device 104 is in fluid communication with IV tube 102 such that fluid drawing device 104 can draw fluid from a patient through IV tube 102 past sample port 106. After fluid drawing device 104 has drawn fluid past sample port 106, fluid sampling device 110 can be introduced into sample port 106 to obtain a fluid sample, as illustrated by the dotted lines shown in FIG. 1.

FIG. 1 illustrates an exemplary embodiment of a fluid drawing device 104, details of which are disclosed in co-pending U.S. patent application Ser. No. 11/765,888, entitled SYSTEMS, METHODS, AND DEVICES FOR SAMPLING BODILY FLUID, which is incorporated herein by reference. It will be appreciated, however, that any device capable of drawing fluid through IV tube 102 past sample port 106 may be used in place of the illustrated fluid drawing device 104. For example, a syringe connected to IV tube 102 can be used to draw fluid from a patient into IV tube 102. Similarly, a VAMP® fluid drawing system made by Edwards Lifesciences Corporation can be used to draw fluid from a patient into IV tube 102.

In use, fluid drawing device 104 is connected to IV tube 102 such that fluid drawing device 104, when activated, is able to draw a patient's bodily fluid through IV tube 102 past sample port 106. The drawing of fluid through IV tube 102 can be accomplished in a variety of ways. For example, when fluid drawing device 104 is activated, a negative pressure can be created within IV tube 102. The negative pressure is sufficient to draw the fluid, such as blood, from a patient into IV tube 102 and past sample port 106. After the bodily fluid has been drawn past sample port 106, the user can then insert fluid sampling device 110 into sample port 106 to retrieve the desired fluid sample.

Figure 2:
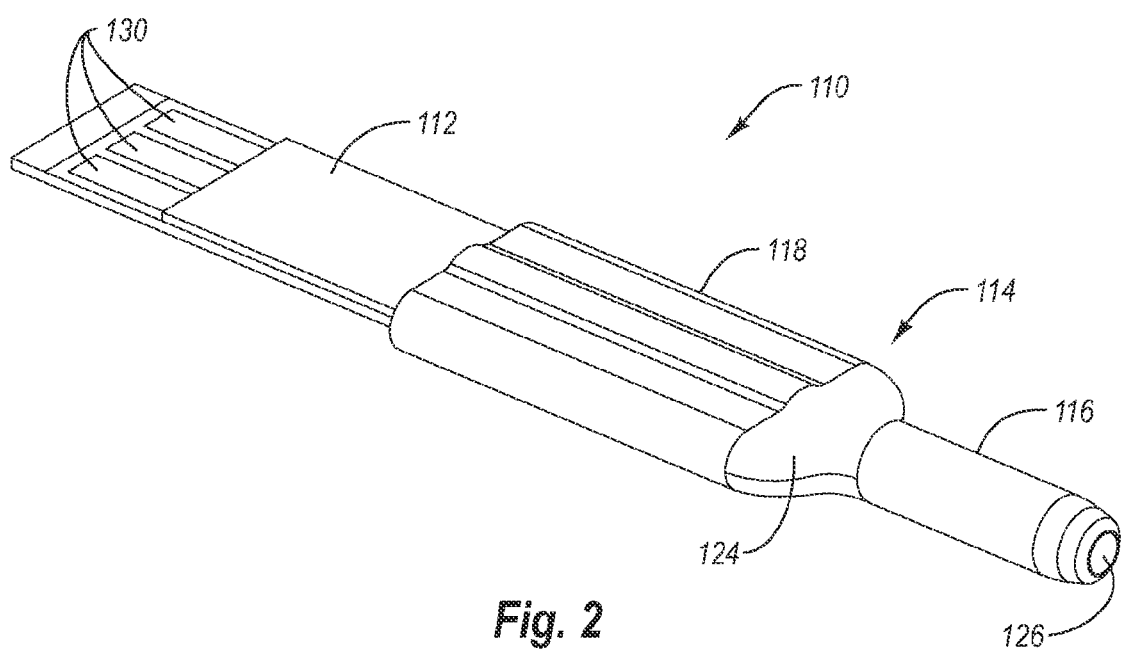
FIG. 2 illustrates a perspective view of a fluid sampling device according to an exemplary embodiment of the present invention.
Figure 3:
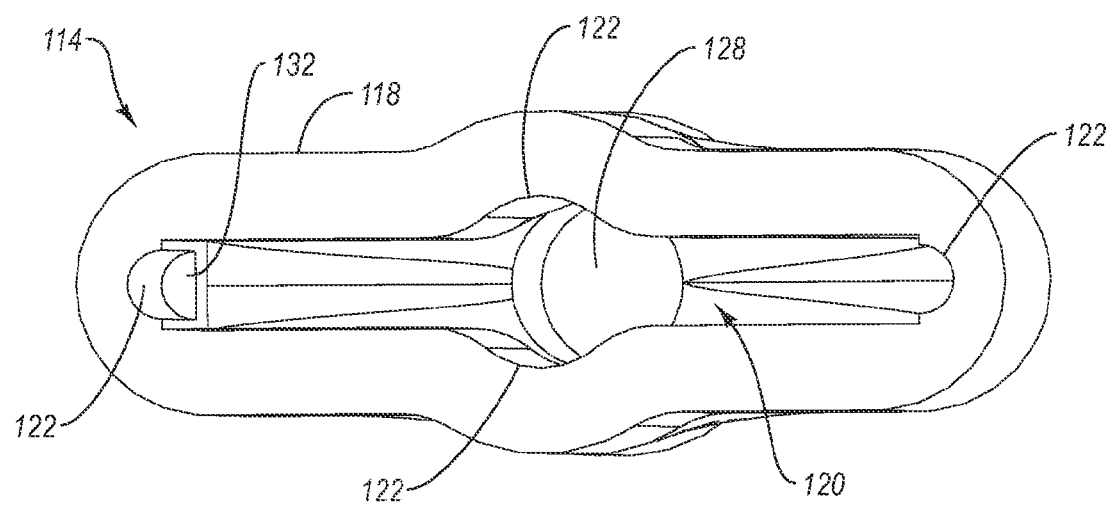
FIG. 3 illustrates a perspective end view of a test strip housing portion of the fluid sampling device of FIG. 2.

FIGS. 2 and 3 illustrate perspective views of an embodiment of fluid sampling device 110. Fluid sampling device 110 comprises a test strip 112 and a test strip adapter 114. Test strip adapter 114 includes a blunt cannula 116 and a test strip housing 118. As illustrated in FIGS. 2 and 3, test strip housing 118 has a generally flat, rectangular shape with a test strip receptacle 120. Test strip receptacle 120 is adapted to receive an end of test strip 112 therein. In the illustrated embodiment, test strip receptacle 120 is sized and configured to generally correspond to the size and shape of test strip 112 such that an end of test strip 112 can be inserted and maintained within test strip receptacle 120 of test strip housing 118 by a variety of means, including frictional coupling, mechanical fasteners such as clamps or pins, and adhesives such as glue. Test strip housing 118, test strip receptacle 120, friction couplings, mechanical fasteners, and adhesives are each examples of means for holding a test strip. In addition, test strip housing 118 can function as a handle to facilitate simple and convenient use of fluid sampling device 110.

As can be seen in FIG. 3, the walls of test strip receptacle 120 include grooves 122 which are adapted to assist in venting air from test strip 112 and test strip receptacle 120 to enable fluid to readily flow into test strip receptacle 120 and/or be absorbed by test strip 112. Grooves 122 are one example of means for venting air from test strip housing 118 and test strip receptacle 120. Additionally, grooves 122 can be adapted to assist in properly aligning test strip 112 when it is being inserted into test strip receptacle 120. Furthermore, grooves 122 can also assist in holding test strip 112 within test strip receptacle 120. Thus, grooves 122 are one example of means for holding test strip 112.

In the exemplary embodiment, grooves 122 extend from the opening of test strip receptacle 120 to about the opposing end of test strip receptacle 120. As illustrated, the opposing end of grooves 122 can include an abutment 132. Abutment 132 can be a means for ensuring proper positioning of test strip 112 within test strip receptacle 120. For example, as test strip 112 is inserted into test strip receptacle 120, abutment 132 can prevent over insertion as well as provide a tactile indication that test strip 112 has been fully inserted. It will be appreciated that grooves 122 can be configured in ways other than those illustrated. For example, grooves 122 can comprise a single groove or multiple grooves, and the size, shape, orientation and positioning of grooves 122 can be altered based, for example, on the type of test strip used with test strip adapter 114.

Test strip 112 can be any one of a variety of test strips having electrical connections 130 or other means for detecting, analyzing and/or conveying properties of a fluid sample received by fluid sampling device 110. For example, test strip 112 could be a ONE TOUCH ULTRA® test strip made by LifeScan (a Johnson & Johnson subsidiary) or a COMFORT CURVE® test strip made by Accu-Chek (a Roche subsidiary). It will be appreciated that test strip 112 is not limited to the above-identified test strips. For example, test strip 112 can comprise an absorbent material, a reagent, and/or electrical leads that are not mounted on a substrate, but which can detect, convey, and/or analyze properties of a fluid sample. Thus, means for detecting, conveying, or analyzing a property of a fluid sample can include any one or more of electrical leads, an absorbent material, and a reagent.

Extending from an end of test strip housing 118 is a tapered portion 124. Tapered portion 124 is generally funnel shaped and connects test strip housing 118 to blunt canula 116. Blunt canula 116 has a lumen 126 extending from a distal end of blunt canula 116 to the interior 128 of tapered portion 124 in order to communicate a fluid sample through test strip adapter 114. Blunt canula 116, lumen 126, tapered portion 124, and interior 128 are each examples of means for communicating a fluid. The distal end of blunt canula 116 is adapted to be inserted into sample port 106 (FIG. 1) to obtain a fluid sample, such as a blood sample. Blunt canula 116 is one example of means for accessing an interior portion of a sample port to obtain a fluid sample.

Fluid sampling device 110 can be made from medical device industry standard plastics including, but not limited to thermoplastics, such as Polyethylene (PE), High Density Polyethylene (HDPE), Polypropylene (PP), Polystyrene (PF), Polyethylene Terephthalate (PET), and acrylic (for transparent properties), because of their low cost production, ability to be easily molded, sterility, and strength.

Fluid sampling device 110 can be formed of multiple discrete parts that are coupled together. For example, test strip housing 118, tapered portion 124, and blunt canula 116 can be made from discrete parts and joined together, such as with an adhesive. Alternatively, fluid sample device 110 can be formed as a single integral piece through a molding process, for example. Additionally, a fluid monitoring device, such as an absorbent material or electrical connections, can be at least partially disposed within or in fluid communication with the test strip receptacle 120 such that various attributes of the fluid sample can be detected without the use of a conventional test strip.

In use, test strip 112 is positioned within test strip receptacle 120 of fluid sampling device 110. After fluid drawing device 104 has been activated and a fluid has been drawn into IV tube 102 past sample port 106, a user can insert the distal end of blunt canula 116 into sample port 106 to obtain a fluid sample. Pressure, such as hydrostatic, hemodynamic, or mechanically induced pressure, causes fluid from sample port 106 to enter lumen 126, move up through blunt canula 116 and tapered portion 124, and onto test strip 112. As noted, grooves 122 are disposed adjacent test strip 112 to facilitate the escape of air from test strip 112 and test strip receptacle 120, thus enabling the fluid sample to readily flow into test strip receptacle 120 and onto test strip 112.

When a sufficient fluid sample has been obtained, fluid sampling device 110 can be removed from sample port 106. Electrical connections 130 of test strip 112 can then be inserted into a glucometer, such as glucometer 200 illustrated in FIG. 4, for analysis. The electrical connections 130 of test strip 112 can be inserted in glucometer 200 after the fluid sample has been obtained. Alternatively, test strip 112 can be inserted into glucometer 200 prior to inserting blunt canula 116 into sample port 106. In this manner, the fluid sample can be obtained and glucometer 200 can begin to analyze the sample immediately, without the intervening step of inserting the test strip 112 into glucometer 200 after obtaining the fluid sample.

Figure 4:
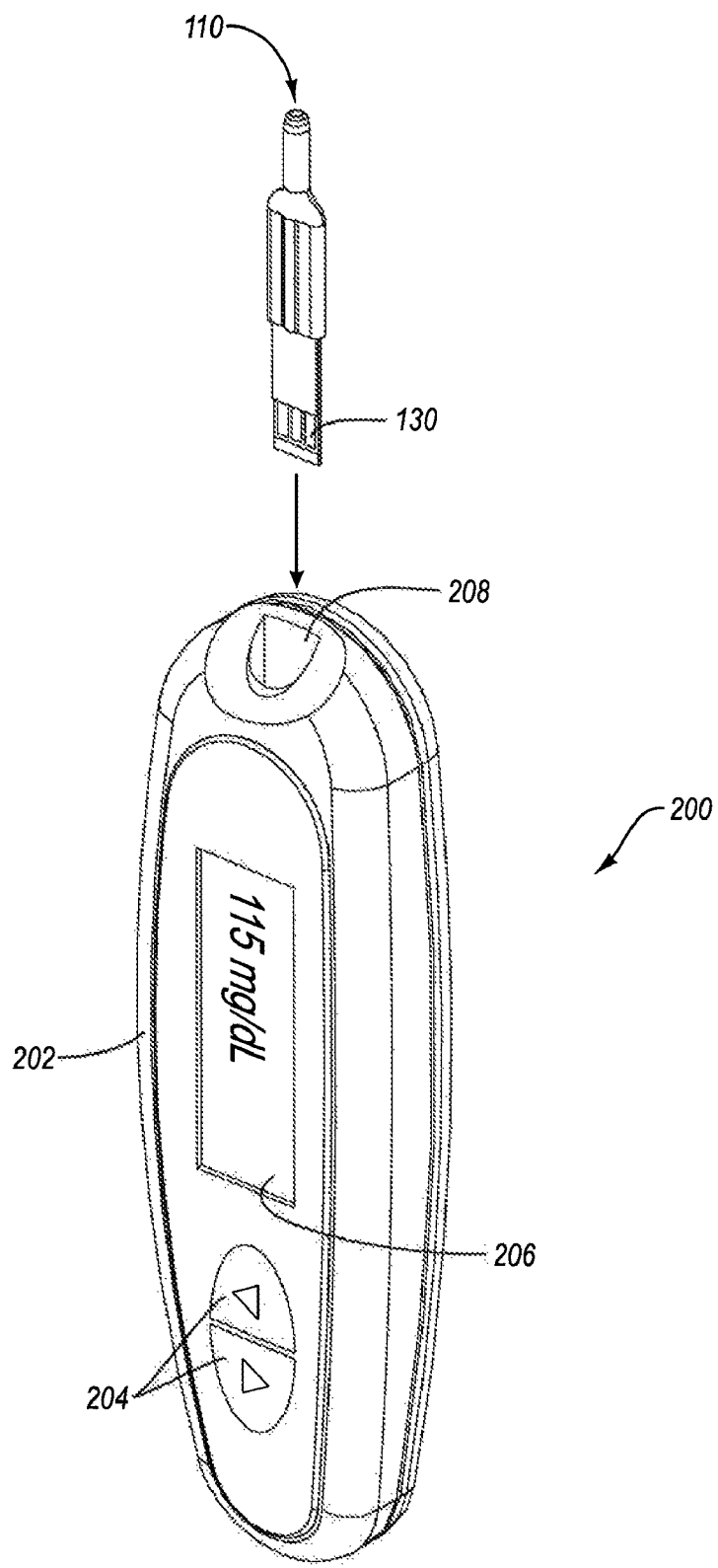
FIG. 4 illustrates an exemplary fluid sampling device according to the present invention associated with a glucometer for analyzing a fluid sample obtained with the fluid sampling device.

Glucometers, such as the one illustrated in FIG. 4, are well known in the art. A typical glucometer 200 comprises a housing 202, keys 204, display 206, internal analysis apparatus (not shown), and a receptacle 208 for receiving a test strip having a fluid sample, such as a blood sample, disposed thereon. The glucometer shown in FIG. 4 has a receptacle 208 that is designed to receive an end of test strip 112 therein. Disposed within receptacle 208 are electrical connections (not shown) which are adapted for electrical communication with electrical connections 130 of test strip 112 when the end of test strip 112 is inserted within receptacle 208. The internal analysis apparatus of glucometer 200 is adapted to analyze various electrical properties of the fluid sample received on test strip 112 and provide the results on display 206. Such electrical properties can include the resistance, impedance, capacitance, and the like of the fluid sample. Glucometer 200 is adapted to determine various attributes of the fluid sample, such as the glucose level of a blood sample, based on the electrical properties of the fluid sample. As noted above, fluid sampling system 100 can employ a glucometer that is adapted to analyze a fluid sample based on non-electrical properties of the fluid sample, including color changes, luminescence, and the like.

Figure 5A:
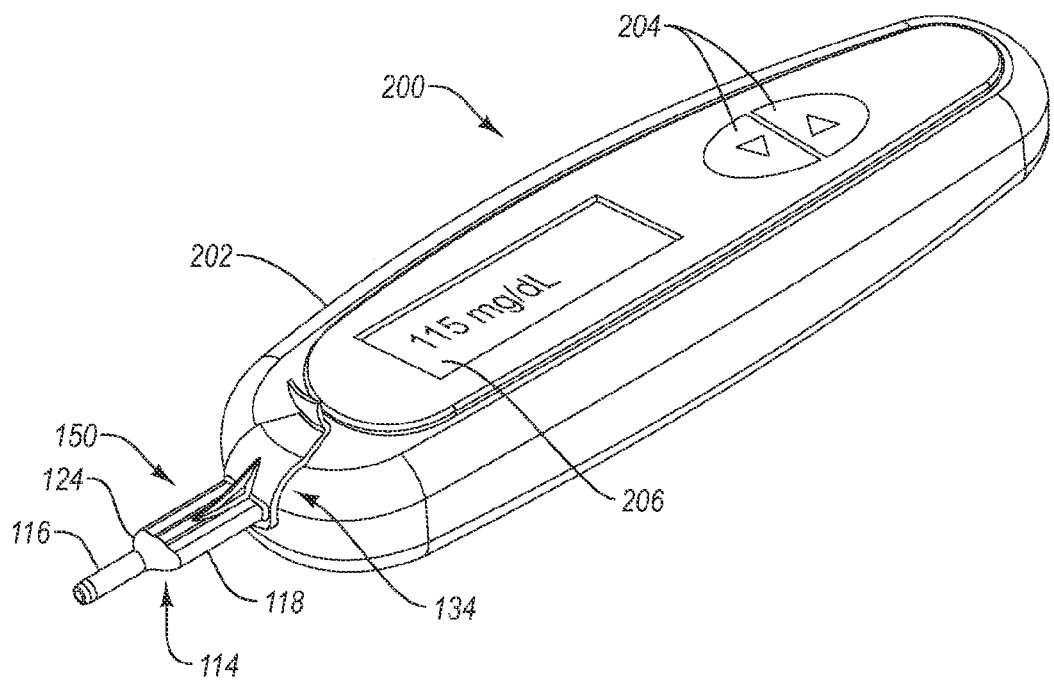
FIG. 5A illustrates a perspective view of another embodiment of the fluid sampling device of the present invention, the fluid sampling device being associated with a glucometer.
Figure 5B:
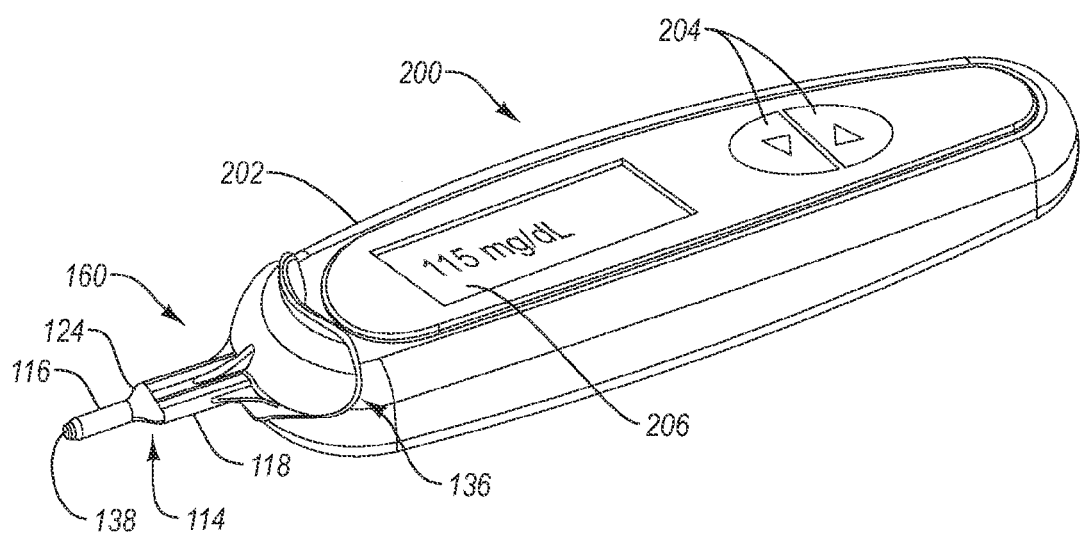
FIG. 5B illustrates a perspective view of yet another embodiment of the fluid sampling device of the present invention, the fluid sampling device being associated with a glucometer.

FIGS. 5A and 5B illustrate alternative embodiments of the fluid sampling device of the present invention. The fluid sampling device 150 of FIG. 5A is similar to fluid sampling device 110. In particular, fluid sampling device 150 includes a test strip adapter 114 that receives a test strip 112 therein. The test strip adapter 114 includes a blunt cannula 116, a test strip housing 118, and a tapered portion 124 similar to those of fluid sampling device 110. In addition, fluid sampling device 150 also includes a tab 134 that extends from the end of test strip housing 118 opposite blunt cannula 116. Tab 134 is shaped and sized to extend around at least a portion of glucometer 200 when fluid sampling device 150 is associated with glucometer 200, as illustrated in FIG. 5A.

Tab 134 is adapted to provide greater stability to fluid sampling device 150 when fluid sampling device 150 is used to obtain a fluid sample from sample port 106. When obtaining a fluid sample with fluid sampling device 150 when it is associated with glucometer 200 as illustrated, glucometer 200 acts as an enlarged handle for fluid sampling device 150. A user holding glucometer 200 can also hold tab 134 with the same hand, thereby providing greater rigidity and stability between glucometer 200 and fluid sampling device 150. Additionally, after the fluid sample has been obtained, tab 134 can be used to remove fluid sampling device 150 from glucometer 200. Specifically, a user can simply push on tab 134 in the direction of blunt canula 116 to disengage fluid sampling device 150 from glucometer 200.

FIG. 5B illustrates an alternative embodiment of stabilizing tab 134. In particular, tab 136 of FIG. 5B extends from fluid sampling device 160 and is larger than tab 134 of FIG. 5A. Tab 136 extends further around the sides of glucometer 200. Tab 136 can provide even greater rigidity and stability between fluid sampling device 160 and glucometer 200.

FIG. 5B also illustrates blunt canula 116 having a one-way valve 138 to prevent or limit the reflux of air into IV tube 102. In the illustrated embodiment, the valve 138 is coupled to the distal end of lumen 126. The valve 138 can also be disposed in other positions within lumen 126. One-way valves suitable for such medical devices are well known in the art. Valve 138 can be made of a medical grade plastic and/or rubber.

Figure 6A:
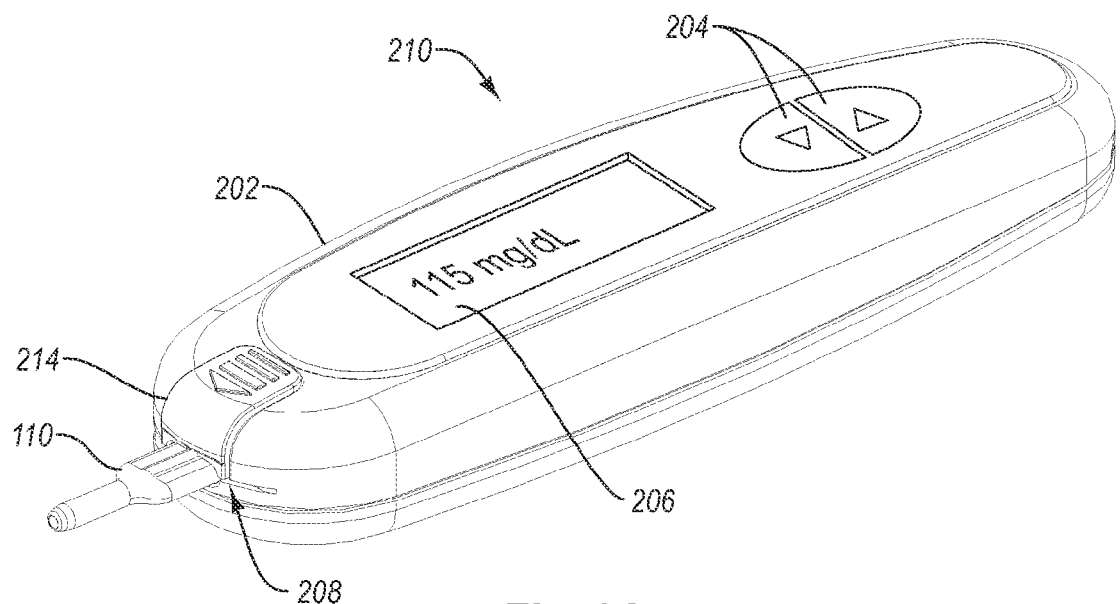
FIG. 6A illustrates a perspective view of the fluid sampling device of FIG. 2 associated with a glucometer having a receptacle for receiving the fluid sampling device and an ejector for removing the fluid sampling device.
Figure 6B:
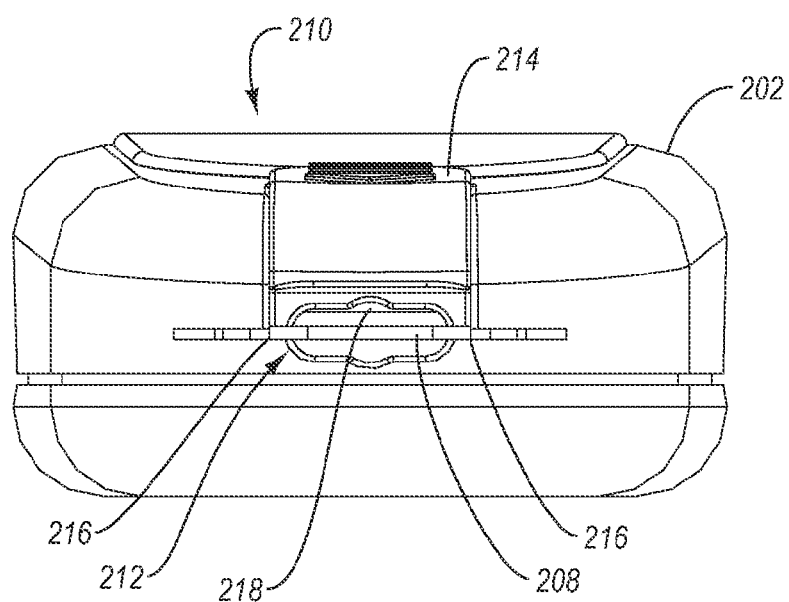
FIG. 6B illustrates an end view of the glucometer of FIG. 6A.
Figure 6C:
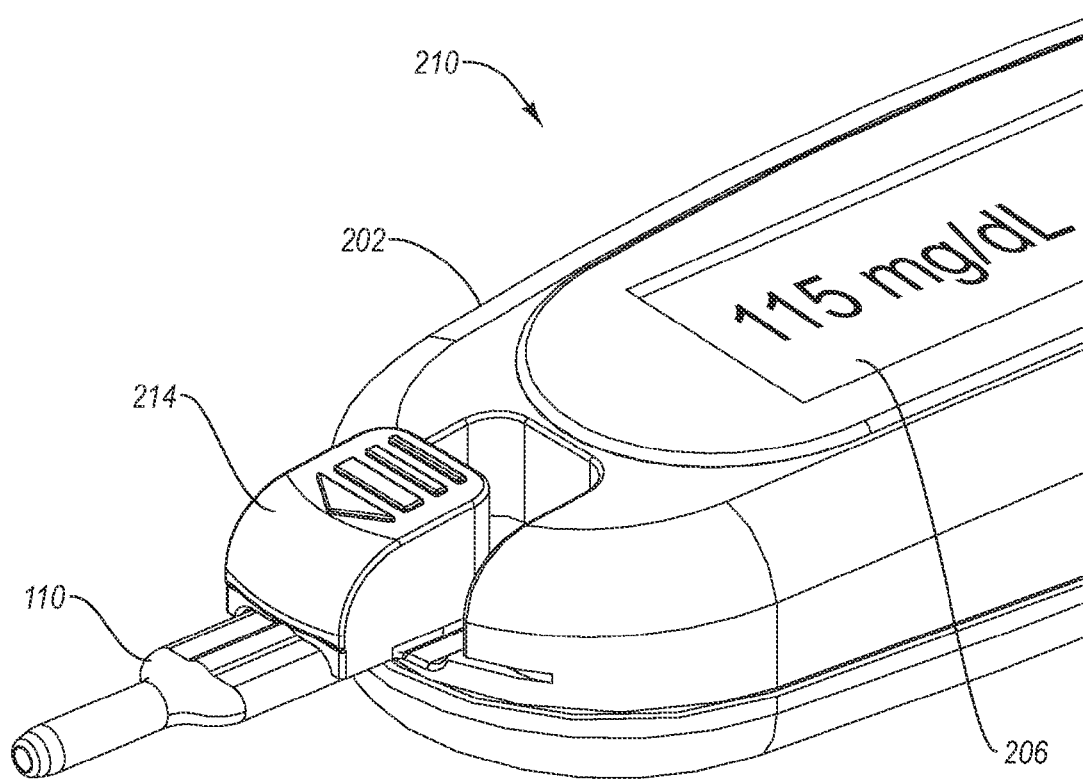
FIG. 6C illustrates a perspective view of the glucometer of FIG. 6A ejecting a fluid sampling device therefrom.

Attention is now directed to FIGS. 6A-6C, in which is illustrated a modified glucometer 210 for use with test strip adapter 110. Similar to glucometer 200, glucometer 210 includes a housing 202, keys 204, display 206, internal analysis apparatus (not shown), and a receptacle 208 for receiving a test strip therein. Disposed within receptacle 208 are electrical connections (not shown) which are adapted for electrical communication with electrical connections 130 of test strip 112 when the end of test strip 112 is inserted within receptacle 208. The internal analysis apparatus of glucometer 210 is adapted to analyze various electrical properties of the fluid sample received on test strip 112 and provide the results on display 206. Such electrical properties can include the resistance, impedance, capacitance, and the like of the fluid sample. Glucometer 210 is adapted to determine various attributes of the fluid sample, such as the glucose level of a blood sample, based on the electrical properties of the fluid sample. As noted above, fluid sampling system 100 can employ a glucometer that is adapted to analyze a fluid sample based on non-electrical properties of the fluid sample, including color changes, luminescence, and the like.

In addition to the above-identified features, glucometer also includes a mechanism for securely coupling together and selectively releasing test strip adapter 110 and glucometer 210. More specifically, glucometer 210 includes a test strip adapter receptacle 212 for receiving an end of test strip adapter 110 therein. Test strip adapter receptacle 212 is formed adjacent test strip receptacle 208 such that when test strip adapter 110 is positioned within test strip adapter receptacle 212, test strip 112 can be positioned within both test strip receptacle 208 of glucometer 210 and test strip receptacle 120 of test strip adapter 110.

As illustrated in FIG. 6B, the interior surface of test strip adapter receptacle 212 is configured to generally conform to the exterior surface shape of test strip adapter 110. The complimentary shapes of test strip adapter 110 and test strip adapter receptacle 212 facilitates the secure engagement of test strip adapter 110 within test strip adapter receptacle 212 during use. More specifically, the shape of test strip adapter receptacle 212 prevents test strip adapter 110 from moving relative to glucometer 210 when glucometer 210 and test strip adapter 110 are used to obtain a fluid sample. Thus, the configuration of test strip adapter receptacle 212 is adapted to maintain a desired orientation of test strip adapter 110 relative to glucometer 210.

Test strip adaptor receptacle 212 is formed by housing 202 and an ejector 214. In the illustrated embodiment, housing 202 forms the lower half of test strip adaptor receptacle 212, while ejector 214 forms the upper half of test strip adaptor receptacle 212. Housing 202 and ejector 214 also cooperate to form channels 216 on opposing sides of test strip adaptor receptacle 212. Channels 216, similar to grooves 122 described above, assist in venting air from test strip 112, test strip receptacle 120, and test strip adapter receptacle 212 to enable fluid to readily flow into test strip receptacle 120 and/or test strip 112. Channels 216 are, therefore, one example of means for venting air from test strip housing 118 and test strip receptacle 120.

In addition to assisting in maintaining the position and orientation of test strip adapter 110 within test strip adapter receptacle 212, ejector 214 also facilitates removal of test strip adapter 110 and/or test strip 112 from glucometer 210. Ejector 214 is movably coupled to housing 202 of glucometer 210. As illustrated in FIG. 6C, ejector 214 can be slidably or otherwise coupled to housing 202 such that ejector 214 can move relative to housing 202 in a direction generally parallel to a longitudinal axis of housing 202.

When ejector 214 is in a receiving position as illustrated in FIG. 6A, test strip adapter 110 can be inserted and maintained within test strip adapter receptacle 212 as described herein. As noted, ejector 214 can be moved relative to housing 202 as illustrated in FIG. 6C. By moving ejector 214 as shown in FIG. 6C, test strip adapter 110 is made readily removable from test strip adapter receptacle 212. In particular, ejector 214 includes a ridge 218 that engages a rear surface of test strip adapter 110. As ejector 214 is moved to the position shown in FIG. 6C, ridge 218 pushes against the rear surface of test strip adapter 110, thereby pushing test strip adapter in the same direction that ejector 214 is moving.

Ejector 214 can be configured to completely remove test strip adapter 110 from test strip adapter receptacle 212 without requiring a user to touch test strip adapter 110. In particular, a user simply moves ejector 214 to the position shown in FIG. 6C, at which point test strip adapter 110 would no longer be within test strip adapter receptacle 212 and test strip adapter 110 would disengage from glucometer 210. Alternatively, ejector 214 can be adapted to partially remove test strip adapter 110 from test strip adapter receptacle 212. For example, a user could move ejector 214 to the position shown in FIG. 6C, which would slide test strip adapter 110 out of test strip adapter receptacle 212 far enough that a user could easily remove test strip adapter 110 from glucometer 210.

Ejector 214 can be biased towards the receiving position illustrated in FIG. 6A. In particular, ejector 214 can be biased such that prior to inserting test strip adapter 110 into test strip adapter receptacle 212, ejector 214 is held in the receiving position illustrated in FIG. 1 so that test strip adapter 110 can be inserted into test strip adapter receptacle 212 as described above. Similarly, after obtaining a fluid sample and removing test strip adapter 110 using ejector 214, ejector 214 can be biased back toward the receiving position shown in FIG. 6A. Ejector 214 can be biased with any suitable biasing means, including springs such as coil springs, leaf springs, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a glucose monitoring system adapted for monitoring blood glucose, in which the glucose monitoring system includes a glucometer and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, an improved blood sampling device for coupling to the sample port to permit a blood sample to be deposited onto a test strip for analyzing blood glucose levels, the improved blood sampling device comprising in combination:

the test strip having one end comprised of an absorbent material and a reagent adapted for detecting blood characteristics indicative of glucose levels, and another end comprised of electrical leads adapted for electronic coupling to the glucometer; and a test strip adapter configured for coupling the test strip in fluid communication with the sampling port of the intravenous line, the test strip adapter comprising:

a housing which comprises a receptacle for the test strip, the housing comprising:

one end joined to a blunt cannula configured for insertion into the sampling port, the blunt cannula being configured to provide fluid communication of a blood sample from the sampling port into the housing receptacle;

an opposite end with an unsealed opening configured to receive said test strip end comprised of the absorbent material and reagent; and said opposite end of the housing terminating at a point that is adapted to permit coupling of the test strip end comprised of electrical leads to the glucometer when the test strip is inserted in said receptacle without having to remove the test strip from the housing.

2. The blood sampling device of claim 1 wherein said test strip adapter further comprises grooves longitudinally within said receptacle at opposite sides thereof and which are configured to assist in venting air from the test strip to enable blood to readily flow into the receptacle in order to contact said test strip.

3. The blood sampling device of claim 2 wherein said grooves are adapted to assist in aligning said test strip in the receptacle.

4. The blood sampling device of claim 2 wherein said grooves are adapted to assist in holding the test strip within the receptacle.

5. The blood sampling device of claim 2 further comprising an abutment at opposing ends of each groove to assist in positioning the test strip within the receptacle by providing a tactile indication that the test strip has been fully inserted into the receptacle.

6. The blood sampling device of claim 1, wherein said housing is joined to said blunt cannula by a tapered portion of the housing.

7. The blood sampling device of claim 1 wherein said housing has a length and width so that the housing is also configured as a handle for inserting or removing the test strip adapter into or from the sampling port of the intravenous system or the glucometer, as desired.

8. The blood sampling device of claim 1 further comprising a tab at said opposite end of the housing terminating at said point which is shy of the test strip end comprised of electrical leads, the tab being configured to extend around at least a portion of the glucometer so that the glucometer is configured as an enlarged handle for the blood sampling device when inserting the device into the sample port to obtain a blood sample.

9. In a blood monitoring system adapted for monitoring blood parameters, in which the blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device,
- a test strip adapter configured for coupling the test strip in fluid communication with the sampling port of the intravenous line, the test strip adapter comprising:
  - a housing which comprises a receptacle configured to receive the test strip;
  - one end of said housing joined to a blunt cannula configured for insertion into the sampling port, the blunt cannula being configured to provide fluid communication of a blood sample from the sampling port into the housing receptacle;
  - an opposite end of said housing having an unsealed opening configured to receive said test strip end configured for contacting the blood sample; and
  - said opposite end of the housing terminating at a point that is adapted to permit a portion of the test strip with the end adapted for coupling to the metering device to be exposed when the test strip is inserted in said receptacle so as to be capable of insertion into the metering device without having to remove the test strip from the housing.

10. The blood sampling device of claim 9 wherein said test strip adapter further comprises grooves longitudinally within said receptacle at opposite sides thereof and which are configured to assist in venting air from the test strip to enable blood to readily flow into the receptacle in order to contact said test strip.

11. The blood sampling device of claim 10 wherein said grooves are adapted to assist in aligning said test strip in the receptacle.

12. The blood sampling device of claim 11 wherein said grooves are adapted to assist in holding the test strip within the receptacle.

13. The blood sampling device of claim 12 further comprising an abutment at opposing ends of each groove, each abutment being adapted to assist in positioning the test strip within the receptacle by providing a tactile indication that the test strip has been fully inserted into the receptacle.

14. The blood sampling device of claim 9, wherein said housing is joined to said blunt cannula by a tapered portion of the housing.

15. The blood sampling device of claim 14 wherein said housing has a length and width so that the housing is also configured as a handle for inserting or removing the test strip adapter into or from the sampling port of the intravenous system or the metering device, as desired.

16. The blood sampling device of claim 15 further comprising a tab at said opposite end of the housing terminating at said point that is adapted to permit a portion of the test strip end with the end adapted for coupling to the metering device to be exposed so as to be capable of insertion into the metering device, the tab being configured to extend around at least a portion of the metering device so that the metering device is configured to serve as an enlarged handle for the blood sampling device when inserting the device into the sample port to obtain a blood sample.

17. A method for monitoring blood parameters, in which a blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device,
- the method comprising:
  - obtaining a test strip adapter configured for coupling the test strip in fluid communication with the sampling port of the intravenous line, the test strip adapter comprising:
    - a housing which comprises a receptacle configured to receive the test strip;
    - one end of said housing joined to a blunt cannula configured for insertion into the sampling port, the blunt cannula being configured to provide fluid communication of a blood sample from the sampling port into the housing receptacle;
    - an opposite end of said housing having an unsealed opening configured to receive said test strip end configured for contacting the blood sample; and
    - said opposite end of the housing terminating at a point that is adapted to permit a portion of the test strip with the end adapted for coupling to the metering device to be exposed when the test strip is inserted in said receptacle so as to be capable of insertion into the metering device without having to remove the test strip from the housing;

inserting the test strip end configured for contacting the blood sample into the receptacle of the housing through said opposite end of said housing;

after blood is withdrawn from the patient into the fluid drawing device and sample port, inserting the blunt cannula into the sample port to obtain a blood sample on the test strip;

removing the test strip adapter with the inserted test strip from the sample port; and without removing the test strip from the adapter, inserting the exposed end of the test strip into the metering device.

18. A method for monitoring blood parameters, in which a blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device, the method comprising:

obtaining a test strip adapter configured for coupling the test strip in fluid communication with the sampling port of the intravenous line, the test strip adapter comprising:

a housing which comprises a receptacle configured to receive the test strip;

one end of said housing joined to a blunt cannula configured for insertion into the sampling port, the blunt cannula being configured to provide fluid communication of a blood sample from the sampling port into the housing receptacle;

an opposite end of said housing having an unsealed opening configured to receive said test strip end configured for contacting the blood sample; and said opposite end of the housing terminating at a point that is adapted to permit a portion of the test strip with the end adapted for coupling to the metering device to be exposed when the test strip is inserted in said receptacle so as to be capable of insertion into the metering device without having to remove the test strip from the housing;

inserting the test strip end configured for contacting the blood sample into the receptacle of the housing through said opposite end of said housing;

without removing the test strip from the adapter, inserting the exposed end of the test strip into the metering device; and after blood is withdrawn from the patient into the fluid drawing device and sample port, and with the metering device still containing the test strip adapter with the inserted test strip, grasping the metering device and inserting the blunt cannula into the sample port to obtain a blood sample on the test strip.

* * * * *